| United States Patent [19] | [11] Patent Number: 4,954,284 |
| Batt et al. | [45] Date of Patent: Sep. 4, 1990 |

[54] AZEOTROPE-LIKE COMPOSITIONS OF DICHLORO-TRIFLUOROETHANE AND ETHYLENE OXIDE

[75] Inventors: James A. Batt, Depew; Robert G. Richard, Cheektowaga; Ian R. Shankland; David P. Wilson, both of Williamsville, all of N.Y.

[73] Assignee: Allied-Signal Inc., Morris Township, N.J.

[21] Appl. No.: 400,607

[22] Filed: Aug. 30, 1989

Related U.S. Application Data

[63] Continuation-in-part of Ser. No. 251,729, Oct. 3, 1988, abandoned.

[51] Int. Cl.$^5$ .......................... C11D 7/30; C11D 7/50
[52] U.S. Cl. ..................................... 252/170; 252/162; 252/172; 252/364; 252/DIG. 9; 203/67; 422/34; 422/37
[58] Field of Search .............. 252/162, 170, 172, 364, 252/DIG. 9; 203/67; 422/34, 37

[56] References Cited

U.S. PATENT DOCUMENTS

| 3,068,064 | 12/1962 | McDonald | 21/58 |
| 3,589,861 | 6/1971 | Gunther | 21/58 |
| 4,816,176 | 3/1989 | Lund | 252/171 |

FOREIGN PATENT DOCUMENTS

| 0128945 | 3/1989 | Japan . |
| 0056630 | 5/1989 | Japan . |

*Primary Examiner*—Paul Lieberman
*Assistant Examiner*—Kathleen Markowski
*Attorney, Agent, or Firm*—Colleen D. Szuch; J. P. Friedenson

[57] ABSTRACT

Azeotrope-like compositions comprising ethylene oxide and dichlorotrifluoroethane isomers or mixtures thereof are novel constant boiling compositions which are useful as sterilizing gases.

17 Claims, No Drawings

AZEOTROPE-LIKE COMPOSITIONS OF DICHLORO-TRIFLUOROETHANE AND ETHYLENE OXIDE

This application is a continuation-in-part of application Ser. NO. 251,729, filed Oct. 3, 1988, now abandoned.

FIELD OF THE INVENTION

This invention relates to novel azeotrope-like mixtures of dichlorotrifluoroethane and ethylene oxide. These mixtures are useful as gaseous sterilizing agents.

BACKGROUND OF THE INVENTION

Sterilization with a germicidal agent, such as ethylene oxide gas or ethylene oxide gas mixtures, has played an increasingly important role in sterilizing heat or moisture sensitive materials. Rapid growth in the use of sterile, disposable medical devices is just one consequence of gaseous sterilization with agents such as ethylene oxide. The basic gaseous sterilization process consists of evacuating the sterilization chamber, preconditioning the articles to be sterilized at an optimal relative humidity, generally between 20–70% RH, admitting the sterilizing gas at an appropriate pressure and temperature, maintaining contact between the sterilizing atmosphere and the articles to be sterilized for an appropriate time and finally discharging and evacuating the chamber to remove the sterilant gas.

Although there are many variations on the basic process, the major factors which have to be controlled in order to effect the sterilization are exposure time, temperature, ethylene oxide pressure or partial pressure and relative humidity. The following prior art references provide a good description of the standard sterilization processes and apparatus with which the gaseous sterilizing agents of the invention are useful: "Principles and Method of Sterilization," pp. 501–530, 2nd Ed. (1969) by J. J. Perkins; "Ethylene Oxide Gaseous Sterilization for Industrial Applications," pp. 181–208, in Industrial Sterilization International Symposium, 1972; U.S. Pat. No. 3,068,064 and U.S. Pat. No. 3,589,861.

Ethylene oxide by itself is an extremely flammable gas, its flammability range extends from about 3.5% by volume to 100% by volume in air. When using ethylene oxide alone as a sterilizing gas, precautions such as explosion proof equipment are mandatory.

A preferable practice is to blend the ethylene oxide with another fluid which is inert as far as the sterilizing process is concerned, but serves to dilute the ethylene oxide and render the mixture as a whole nonflammable. Two such blends which have been used as sterilizing gases are dichlorodifluoromethane (CFC-12)/ethylene oxide and carbon dioxide/ethylene oxide. These blends are non-azeotropic in nature and therefore suffer the disadvantage of segregation during vaporization which could lead to potentially flammable or explosive situations if process flow rates, outage volumes, etc. are not closely monitored and controlled.

The CFC-12/ethylene oxide blend is generally supplied as a liquid mixture consisting of 88% by weight CFC-12 and 12% by weight ethylene oxide. This composition is below the critical flammability composition of about 14–15% by weight ethylene oxide in CFC-12, and is therefore nonflammable. A typical hospital sterilization process which utilizes the CFC-12/ethylene oxide blend is performed by evacuating the chamber to about 20–24 inches of mercury vacuum and filling the chamber to about 10 psig pressure with the gas mixture after completinq the humidification step. Sterilization is generally performed around 130° F. This procedure provides up to about 630 milligrams of ethylene oxide per liter.

A disadvantage of using CFC-12 in such mixtures is that fully halogenated chlorofluorocarbons such as CFC-12 are suspected of causing environmental problems in connection with the earth's protective ozone layer.

Although the major purpose of the inert component in these sterilizing gas mixtures is to mask the flammability characteristics of ethylene oxide, simple substitution of an arbitrary nonflammable diluent does not necessarily ensure a useful sterilizing gas mixture. First, the flammability properties of the blend must be such that sufficient ethylene oxide (mg/liter at a typical pressure and temperature) is delivered by the blend to affect the sterilization in an appropriate time. If the diluent does not mask the flammability to a sufficient extent, a lower concentration of ethylene oxide must be used to ensure nonflammability, and either a longer time period is required to perform the sterilization, which affects productivity, or greater operating pressures are required to increase the effective ethylene oxide density in the sterilization chamber. Increasing the operating pressure is generally not a viable option because existing sterilization chambers may not be rated for the increased pressure and, as pointed out by Gunther in U.S. Pat. No. 3,589,861, increased pressure can lead to swelling and rupture of the sealed plastic bags commonly used to package disposable medical devices. Indeed, lower operating pressures are advantageous in this respect.

A candidate inert diluent should preferably also be miscible with ethylene oxide in the liquid phase and should not be too highly volatile that it would segregate from the ethylene oxide to any great extent during vaporization. Segregation or fractionation can lead to potentially flammable or explosive situations. An azeotrope-like mixture would be useful in this context as it does not fractionate by normal evaporation or distillation processes thereby resulting in release of the flammable ethylene oxide component.

It is accordingly an object of this invention to provide a novel sterilizing gas mixture containing ethylene oxide.

It is another object of the invention to provide such a sterilizing gas mixture which contains an inert fluorocarbon diluent which is considered to be stratospherically safe.

Another object of the invention is to provide such a sterilizing gas mixture in which the fluorocarbon is miscible with the ethylene oxide and which mixture is azeotropic or non-segregating.

Still another object of the invention is to provide a novel sterilizing gas mixture which incorporates all of the above stated objectives.

Other objects and advantages of the invention will become apparent from the following description of the invention.

SUMMARY OF THE INVENTION

In accordance with the invention novel azeotropelike compositions are provided comprising dichlorotrifluoroethane and ethylene oxide. These compositions are useful as sterilizing gases. Such azeotrope-like compositions are formed when either isomer of dichlorotrifluoroethane is employed or when mixtures of dichlorotrifluoroethane are employed in any proportions.

DETAILED DESCRIPTION OF THE INVENTION AND OF THE PREFERRED EMBODIMENTS

Dichlorotrifluoroethane, not being perhalogenated, is considered to be stratospherically safe. Both isomers, 1,1-dichloro-2,2,2-trifluoroethane (HCFC-123) and 1,2-dichloro-1,2,2-trifluoroethane (HCFC-123a). have much shorter atmospheric life times and consequently possess a much lower ozone depletion potential than the fully halogenated CFC-12. Atmospheric models indicate that HCFC-123 and HCFC-123a have ozone depletion potential fifty times lower than that of CFC-12.

The vapor or gas mixtures arising from these blends are nonflammable and in certain instances, within the indicated ranges, contain more ethylene oxide on a volume or mole basis than the traditional 88/12 by weight CFC-12/ethylene oxide sterilizing gas mixture. As the novel blends are azeotropes, the potential for fractionation or separation of components through vaporization, leading to mixtures enriched in ethylene oxide possibly becoming flammable or explosive, is much less than is the case with blends of ethylene oxide with CFC-12 or carbon dioxide.

The azeotrope-like compositions of the invention comprise from about 89 weight percent to about 97 weight percent dichlorotrifluoroethane and from about 11 weight percent to about 3 weight percent ethylene oxide.

The preferred isomer is HCFC-123. The preferred form of the HCFC-123 is "commercial HCFC-123" which is available as "pure" HCFC-123 containing about 90 to about 95 weight percent of HCFC-123. about 5 to about 10 weight percent of HCFC-123a, and impurities such as trichloromonofluoromethane, trichlorotrifluoroethane and methylene chloride which due to their presence in insignificant amounts, have no deleterious effects on the properties of the azeotrope-like compositions. Commercial HCFC-123 is also available as "ultra-pure" HCFC-123 which contains about 95 to about 99.5 weight percent of HCFC-123, about 0.5 to about 5 weight percent of HCFC-123a, and impurities as listed above.

In the embodiment of the invention incorporating HCFC-123 or commercial HCFC-123, the azeotropic or constant boiling compositions comprise from about 89 weight percent to about 95 weight percent HCFC-123 or commercial HCFC-123 and from about 11 weight percent to about 5 weight percent ethylene oxide. The most preferred embodiment is the true azeotropic composition. Our best estimate of the true azeotropic composition is about 93.3 weight percent HCFC-123 and about 6.7 weight percent ethylene oxide, which exhibits a boiling point of about 28.8° C. at 744 mm Hg.

In another embodiment of the invention incorporating HCFC-123a, the azeotrope or constant boiling compositions comprise from about 93 weight percent to about 97 weight percent of HCFC-123a and from about 7 weight percent to about 3 weight percent ethylene oxide. The most preferred embodiment is the true azeotropic composition. Our best estimate of the true azeotropic composition is about 96.0 weight percent HCFC-123a and about 4.0 weight percent ethylene oxide, which exhibits a boiling point of about 29.5° C. at 741 mm Hg.

The novel azeotrope-like compositions of the invention can also be stated to comprise mixtures of ethylene oxide and dichlorotrifluoroethane which boil at about 29.1° C.±0.5 at 741 mm Hg.

The precise or true azeotropic compositions have not been determined but have been ascertained to be within the above indicated ranges. Regardless of where the true azeotrope lies, all compositions within the indicated ranges, as well as certain compositions outside the indicated ranges, are azeotrope-like, as defined more particularly below.

Vapor compositions within the azeotrope-like regions for both systems do not exhibit flame limits in air at ambient conditions as determined by the ASTM E 681-79 method.

From fundamental principles, the thermodynamic state of a fluid is defined by four variables: pressure, temperature, liquid composition and vapor composition or P-T-X-Y, respectively. An azeotrope is a unique characteristic of a system of two or more components where X and Y are equal at the stated P and T. In practice this means that the components cannot be separated during evaporation or boiling and consequently it is not possible to separate the flammable ethylene oxide component from the blend by evaporation which could happen if the blend were not azeotrope-like leading to a potentially hazardous situation.

For the purposes of this discussion, by azeotropelike composition is intended to mean that the composition behaves like a true azeotrope in terms of its constant boiling characteristics or tendency not to fractionate upon boiling or evaporation. Such compositions may or may not be a true azeotrope. Thus, in such systems, the composition of the vapor formed during boiling or evaporation is identical or substantially identical to the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

If the vapor and liquid phases have identical compositions, then it can be shown, on a rigorous thermodynamic basis, that the boiling point versus composition curve passes through an absolute minimum or absolute maximum at this composition. If one of the two conditions, identical liquid and vapor compositions or a minimum or maximum boiling point, are shown to exist, then the system is an azeotrope, and the other condition must follow.

Thus, one way to determine whether a candidate mixture is "azeotrope-like" within the meaning of this invention is to distill a sample thereof under conditions (i.e. resolution—number of plates) which would be expected to separate the mixture into its separate components. If the mixture is non-azeotropic or non-azeotrope-like, the mixture will fractionate, i.e. separate into its various components with the lower boiling component distilling off first and so on. If the mixture is azeotrope-like, some finite amount of a first distillation cut will be obtained which contains all of the mixture components and which is constant boiling and behaves as a single substance. This phenomenon cannot occur if the mixture is not azeotrope-like i.e. it is not part of an azeotropic system. If the degree of fractionation of the candidate mixture is unduly great, then a composition closer to the true azeotrope must be selected to minimize fractionation.

An equivalent method for determining whether a candidate mixture is azeotrope-like is to determine whether the boiling point versus composition curve passes through a maximum or minimum. Azeotropes which possess a minimum boiling point also possess a maximum in the vapor pressure curve at the same composition; as these blends exhibit positive deviations from Raoult's Law they are termed positive azeotropes. Similarly, those azeotropes which show a maximum boiling point exhibit a minimum in the vapor pressure curve and are termed negative azeotropes owing to the negative deviations from Raoult's Law. The latter occur much less frequently in nature than the positive azeotropes.

It follows from the above that another characteristic of azeotrope-like compositions is that there is a range of compositions containing the same components in varying proportions which are azeotrope-like. All such compositions are intended to be covered by the term azeotrope-like as used herein. As an example, it is well known that at differing pressures, the composition of a given azeotrope will vary at least slightly as does the boiling point of the composition. Thus, an azeotrope of A and B represents a unique type of relationship but with a variable composition depending on temperature and/or pressure.

One difference between the HCFC-123/ethylene oxide and HCFC-123/ethylene oxide blends and the conventional CFC-12/ethylene oxide sterilant gas is the vapor pressure of the blends. The CFC-12/ethylene oxide blend is more volatile and has a greater vapor pressure. Because of this difference it may be necessary to add a more volatile component to the HCFC-123 or HCFC-123a system simply to serve as a propellant to facilitate delivery of the liquid mixture from the cylinder. Such volatile component should have a higher vapor pressure than the HCFC-123 or HCFC-123a system and be stable and inert to the other components in the sterilant gas mixture. Examples of such propellants are inert gases such as nitrogen, carbon dioxide, sulfur hexafluoride, perchlorofluorocarbons and hydrochlorofluorocarbons, such as chlorodifluoromethane or dichlorodifluoromethane. Others will readily occur to persons of ordinary skill in the art. The addition of other components to the systems which do not change the essential nature and properties of the systems may be deemed necessary or desirable in specific circumstances.

In the process embodiment of the invention, the azeotrope-like compositions of the invention may be used as sterilizing gases in any manner well known in the art by essentially exposing the article to be sterilized to the sterilizing gas under conditions and for a period of time necessary to achieve a desired degree of sterilization. Typically, the process is effected by placing the articles to be sterilized in a chamber, evacuating the chamber, humidifying the chamber and exposing the articles to the sterilizing gas for an appropriate period of time.

In the following Examples, the HCFC-123 or HCFC-123a materials referred to are 99.9% or more pure.

EXAMPLE 1

This example shows that a maximum occurs in the boiling point versus composition curve for both the HCFC123/ethylene oxide system as well the HCFC-123a/ethylene oxide system, confirming the existence of an azeotrope in each case. Boiling point data are also used to define the constant boiling azeotrope-like region in each case.

The temperature of a boiling liquid mixture was measured using an ebulliometric technique similar to that described by W. Swietoslawski in *Ebulliometric Measurements*. p. 4, Reinhold Publishing Corp. (1945).

The ebulliometer was first charged with a weighed amount of HCFC-123. The system was brought to total reflux by placing the lower part of the ebulliometer in a heated water bath. A Cottrell pump aided in delivering slugs of boiling liquid and vapor over a thermowell which contained a precision 25 ohm platinum resistance thermometer. The thermometer recorded the boiling point measurements with a precision of ±0.001° C. Boiling temperature and atmospheric pressure were recorded after steady-state had been attained. A weighed aliquot of ethylene oxide was then introduced into the ebulliometer and the temperature and pressure recorded again after the attainment of steady-state.

The following Table I lists the boiling point measurements at 744 mmHg for various mixtures of HCFC-123 and ethylene oxide.

TABLE I

| | Liquid Mixture | |
|---|---|---|
| Mole Percent Composition 1,1-dichloro-2,2,2-trifluoroethane | Mole Percent Composition ethylene oxide | Boiling Point (°C.) at 744 mmHg |
| 100.0 | 0. | 27.06 |
| 95.3 | 4.7 | 27.51 |
| 89.6 | 10.4 | 28.26 |
| 83.0 | 17.0 | 28.74 |
| 77.1 | 22.9 | 28.83 |
| 73.9 | 26.1 | 28.67 |
| 70.7 | 29.3 | 28.43 |
| 66.6 | 33.4 | 27.88 |
| 64.0 | 36.0 | 27.42 |
| 61.6 | 38.4 | 26.91 |

Interpolation of these data that HCFC-123 and ethylene oxide mixtures exhibit a maximum boiling point of about 28.8° C. at 744 mmHg in the region of 20 mole percent. or about 6.7 weight percent ethylene oxide. Furthermore, compositions in the range 17 to about 29 mole percent (5.5 to about 10.5 weight percent) ethylene oxide boil within about ±0.1° C. of the maximum boiling point, that is, are essentially constant boiling compositions.

A similar series of boiling point determinations were performed for the HCFC-123a and ethylene oxide system. These results are summarized in Table II.

TABLE II

| | Liquid Mixture | |
|---|---|---|
| Mole Percent Composition 1,2-dichloro-1,2,2-trifluoroethane | Mole Percent Composition ethylene oxide | Boiling Point (°C.) at 741 mmHg |
| 100.0 | 0. | 29.09 |
| 97.1 | 2.9 | 29.25 |
| 92.0 | 8.0 | 29.44 |
| 87.4 | 12.6 | 29.52 |
| 85.0 | 15.0 | 29.53 |
| 81.4 | 18.6 | 29.44 |
| 78.7 | 22.3 | 29.26 |
| 64.3 | 35.7 | 28.99 |

These mixtures also exhibit a maximum boiling point of about 29.5° C. at 741 mmHg at about 12.6 mole percent (4.0 weight percent) ethylene oxide. This system is constant boiling to within ±0.1° C. of the maximum over the range 8-20 mole percent (2.4-6.7 weight percent) ethylene oxide.

Because the boiling point versus composition data exhibit an absolute maximum in each case, both HCFC123/ethylene oxide and HCFC-123a/ethylene oxide form negative azeotropes.

EXAMPLE 2

The vapor flammability properties of the various ethylene oxide blends are assessed in this example.

Vapor flammability data were measured at 1 atmosphere pressure and ambient temperature using the ASTM E 681-79 method with an ignition source consisting of a high voltage spark gap. The ternary flammability diagram was mapped by preparing mixtures of ethylene oxide, fluorocarbon and air by the method of partial pressures and then determining whether or not a flame would propagate as defined by ASTM E 681-79. The critical flammability ratio (or composition). i.e. the composition of the fluorocarbon/ethylene oxide blend which contains the maximum proportion of ethylene oxide, yet does not exhibit flame limits in air, was determined in a graphical manner similar to that described by Haenni et al. in Industrial and Engineering Chemistry. Vol. 51. pp. 685-688 (1959).

Critical flammability compositions for mixtures of ethylene oxide with each of CFC-12, HCFC-123 and HCFC-123a are listed in Table III.

TABLE III

| Fluorocarbon | Mole % ethylene oxide | Weight % ethylene oxide |
|---|---|---|
| CFC-12 | 33.3 | 15.4 |
| HCFC-123 | 35.4 | 13.6 |
| HCFC-123a | 34.2 | 13.0 |

The critical flammability composition for CFC-12/ethylene oxide was found to be 15.4 weight percent ethylene oxide which agrees quite well with the work of Haenni et al. who measured 16 weight percent ethylene oxide. The data also indicate that both HCFC-123 and HCFC-123a mask the flammability of ethylene oxide to a slightly greater extent than CFC-12. that is to say these compositions contain more ethylene oxide on a mole basis.

Vapor flammability data also show that the azeotrope-like, constant boiling ranges identified in the previous example are in the nonflammable region, i.e., vapor phases produced by these liquid mixtures have ethylene oxide compositions lower than the critical flammability composition and are nonflammable.

EXAMPLE 3

This example shows that nonflammable, azeotrope-like HCFC-123/ethylene oxide blends make available at least an equivalent amount of gas phase ethylene oxide as does the 88/12 CFC-12/ethylene oxide blend. The quantity of ethylene oxide present in the gas phase is critical to the sterilization process.

The currently commercial 88/12 by weight CFC-12/ethylene lammability composition by about 20%. If, for example, the ethylene oxide composition from the HCFC-123 critical flammability composition is reduced by the same factor for example, a 90 percent by weight HCFC-123 and 10 percent by weight ethylene oxide blend, then the ethylene oxide available in the gas phase from these blends can be compared by performing ideal gas calculations. For this particular example, the assumption shall be made that the sterilization process is performed at a temperature of 130° F. and at a 10 psig pressure, and that the sterilization chamber was initially evacuated to 22 in Hg vacuum. Results of these calculations are summarized in Table IV.

TABLE IV

| | ethylene oxide vapor composition | | |
|---|---|---|---|
| | Weight % | Mole % | mg/liter |
| HCFC-123 ethylene oxide | 10.0 | 27.8 | 645.9 |
| CFC-12/ ethylene oxide | 12.0 | 27.2 | 631.5 |

This table shows that slightly more gaseous ethylene oxide is available for sterilization from the HCFC-123/ethylene oxide blend than from the CFC-12/ethylene oxide blend.

What is claimed is:

1. Azeotrope-like compositions consisting essentially from about 11 weight percent to about 3 weight percent ethylene oxide and from about 89 weight percent to about 97 weight percent dichlorotrifluoroethane selected from the group with of 1,1-dichloro-2,2,2-trifluoroethane and 1,2-dichloro-1,2,2-trifluoroethane, or mixtures thereof, which compositions with 1,1-dichloro2,2,2-trifluoroethane boil at about 28.8° C. at 744 mm Hg, which compositions with 1,2-dichloro-1,2,2,-trifluoroethane boil at about 29.5° C. at 741 mm Hg and which compositions containing a mixture of 1,1-dichloro-2,2,2-trifluoroethane and 1,2-dichloro-1,2,2-trifluoroethane boil at about 29.15° C. at 742.5 mm Hg.

2. Azeotrope-like compositions according to claim, 1 in which the dichlorotrifluoroethane is 1.1-dichloro-2,2,2-trifluoroethane.

3. Azeotrope-like compositions according to claim 1 in which the dichlorotrifluoroethane is 1,2-dichloro-1,2,2-trifluoroethane.

4. Azeotrope-like compositions according to claim 1 consisting essentially of from about 89 weight percent to about 95 weight percent 1,1-dichloro-2,2,2-trifluoroethane and from about 11 weight percent to about 5 weight percent ethylene oxide.

5. Azeotrope-like compositions according to claim 1 consisting essentially of from about 93 weight percent to about 97 weight percent 1.2-dichloro-1,2,2-trifluoroethane and from about 7 weight percent to about 3 weight percent ethylene oxide.

6. Azeotrope-like compositions according to claim 4 consisting essentially of about 93.3 weight percent 1,1-dichloro-2,2,2-trifluoroethane and about 6.7 weight percent ethylene oxide.

7. Azeotrope-like compositions according to claim 5 consisting essentially of about 96.0 weight percent 1,2-dichloro-1,2,2-trifluoroethane and about 4.0 weight percent ethylene oxide.

8. The method of sterilizing articles which comprises exposing the article to a sterilizing gas as defined in claim 1 under conditions and for a period of time necessary to achieve a desired degree of sterilization.

9. The method of sterilizing articles which comprises exposing the article to a sterilizing gas as defined in claim 2 under conditions and for a period of time necessary to achieve a desired degree of sterilization.

10. The method of sterilizing articles which comprises exposing the article to a sterilizing gas as defined in claim 3 under conditions and for a period of time necessary to achieve a desired degree of sterilization.

11. The method of sterilizing articles which comprises exposing the article to a sterilizing gas as defined in claim 4 under conditions and for a period of time necessary to achieve a desired degree of sterilization.

12. The method of sterilizing articles which comprises exposing the article to a sterilizing gas as defined in claim 5 under conditions and for a period of time necessary to achieve a desired degree of sterilization.

13. The method of sterilizing articles which comprises exposing the, article to a sterilizing gas as defined in claim 6 under conditions and for a period of time necessary to achieve a desired degree of sterilization.

14. The method of sterilizing articles which comprises exposing the article to a sterilizing gas as defined in claim 7 under conditions and for a period of time necessary to achieve a desired degree of sterilization.

15. The method according to claim 8 which comprises preconditioning the articles to be sterilized at an optimum relative humidity prior to exposing the articles to the sterilized gas.

16. The method according to claim 8 in which the sterilizing gas is dispensed from a container containing same with the aid of a more volatile fluid.

17. The method according to claim 16 wherein the more volatile fluid is a member selected from the group consisting of nitrogen, carbon dioxide, sulfur hexafluoride, perchlorofluorocarbons and hydrochlorofluorocarbons.

* * * * *